US005718895A

United States Patent [19]

Asgharian et al.

[11] Patent Number: 5,718,895
[45] Date of Patent: Feb. 17, 1998

[54] ENZYMES WITH LOW ISOELECTRIC POINTS FOR USE IN CONTACT LENS CLEANING

[75] Inventors: Bahram Asgharian; Bor-Shyue Hong; Ronald P. Quintana, all of Arlington, Tex.

[73] Assignee: Alcon Laboratories, Inc., Fort Worth, Tex.

[21] Appl. No.: 559,222

[22] Filed: Nov. 16, 1995

[51] Int. Cl.$^6$ .............. A61L 2/00; A61K 38/54; A61K 9/20; D06M 16/00
[52] U.S. Cl. .............. 424/94.1; 424/94.3; 424/464; 422/28; 435/264
[58] Field of Search .............. 424/94.1, 94.3, 424/464; 422/28; 435/264

[56] References Cited

U.S. PATENT DOCUMENTS

| Re. 32,672 | 5/1988 | Huth et al. ............... 252/95 |
| 3,873,696 | 3/1975 | Randeri et al. ............... 424/153 |
| 3,910,296 | 10/1975 | Karageozian et al. ............... 134/2 |
| 3,931,319 | 1/1976 | Green et al. ............... 260/567.6 |
| 4,026,945 | 5/1977 | Green et al. ............... 260/567.6 |
| 4,179,337 | 12/1979 | Davis et al. ............... 435/181 |
| 4,407,791 | 10/1983 | Stark ............... 424/80 |
| 4,414,127 | 11/1983 | Fu ............... 252/95 |
| 4,521,254 | 6/1985 | Anderson et al. ............... 134/26 |
| 4,525,346 | 6/1985 | Stark ............... 424/80 |
| 4,614,549 | 9/1986 | Ogunbiyi et al. ............... 134/19 |
| 4,615,882 | 10/1986 | Stockel ............... 424/80 |
| 4,758,595 | 7/1988 | Ogunbiyi ............... 514/635 |
| 4,836,986 | 6/1989 | Ogunbiyi et al. ............... 422/28 |
| 5,122,614 | 6/1992 | Zalipsky ............... 548/520 |
| 5,576,278 | 11/1996 | Van Duzee et al. ............... 510/114 |

FOREIGN PATENT DOCUMENTS

| 1150907 | 8/1983 | Canada . |
| 0 456 467 A2 | 11/1991 | European Pat. Off. . |
| 0 584 876 A2 | 3/1994 | European Pat. Off. . |
| 57-24526 | 5/1982 | Japan . |
| 86/07264 A1 | 12/1986 | WIPO . |
| 92/17579 A1 | 10/1992 | WIPO . |
| 95/00621 A1 | 1/1995 | WIPO . |
| 95/02044 A1 | 1/1995 | WIPO . |
| 95/07991 | 3/1995 | WIPO . |
| 95/07991 A2 | 3/1995 | WIPO . |

OTHER PUBLICATIONS

Breen et al., "Clinical Comparison of Pancreatin-Based and Subtilisin-Based Enzymatic Cleaners", *Contact Lens Forum*, vol. 15, pp. 32, 34-35, 38 (1990).

Gounaris et al., Some Properties of Succinylated Subtilopeptidase, *Compt. Rend., Trav. Lab. Carlsberg*, vol. 35, pp. 37-62 (1965).

Johansen, Chemical Derivatives of Subtilisins with Modified Proteolytic Activities II. Succinyl- and Glutarylsubtilisin Type Carlsberg, *Compt. Rend. Trav. Lab. Carlsberg*, vol. 37, pp. 145-177 (1970).

Lo, et al., *Journal of The American Optometric Association*, vol. 40, pp. 1106-1109 (1969).

Johansen et al., Chemical derivatives of subtilisin Carlsberg with increased proteolytic activity, *Biochim. Biophys. Acta*, vol. 139, pp. 211-214 (1967).

*Model 111 Mini IEF Cell Instruction Manual*, BIO RAD.

Primary Examiner—Joseph L. Schofer
Assistant Examiner—Kathryne E. Shelborne
Attorney, Agent, or Firm—Michael C. Mayo

[57] ABSTRACT

Compositions containing an ophthalmically acceptable, modified enzyme exhibiting a low pI and methods involving the combined use of these compositions with a polymeric antimicrobial agent, are disclosed for the simultaneous cleaning and disinfecting of contact lens.

14 Claims, No Drawings

ENZYMES WITH LOW ISOELECTRIC POINTS FOR USE IN CONTACT LENS CLEANING

The present invention relates to the field of contact lens cleaning and disinfecting. In particular, this invention relates to compositions containing enzymes which have been modified to exhibit a low isoelectric point and methods for cleaning human-worn contact lenses with those compositions. The invention also relates to methods of simultaneously cleaning and disinfecting contact lenses by combining the enzyme compositions of the present invention with a chemical disinfecting agent.

BACKGROUND OF THE INVENTION

Various compositions and methods for cleaning contact lenses have been described in the patent and scientific literature. Some of these methods have employed compositions containing surfactants or enzymes to facilitate the cleaning of lenses. The first discussion of the use of proteolytic enzymes to clean contact lenses was in an article by Lo, et al. in the *Journal of The American Optometric Association*, volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.).

Numerous compositions and methods for disinfecting contact lenses have also been described. Those methods may be generally characterized as involving the use of heat and/or chemical agents. Representative chemical agents for this purpose include organic antimicrobials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for cleaning and disinfecting contact lenses at the same time have been proposed. Such methods are described in U.S. Pat. Nos. 3,873,696 (Randeri, et al.) and 4,414,127 (Fu), for example. A representative method of simultaneously cleaning and disinfecting contact lenses involving the use of proteolytic enzymes to remove protein deposits and a chemical disinfectant (monomeric quaternary ammonium compounds) is described in Japanese Patent Publication 57-24526 (Boghosian, et al.). The combined use of a biguanide (i.e., chlorhexidine) and enzymes to simultaneously clean and disinfect contact lenses is described in Canadian Patent No. 1,150,907 (Ludwig). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, and commonly assigned U.S. patent application Ser. No. 08/156,043 and in corresponding European Patent Application Publication No. 0 456 467 A2.

Although the use of these enzymatic systems provides effective cleaning, a number of problems associated with their use exist. One problem is that residual amounts of the enzyme can bind to the contact lens. This binding can lead to less clarity of vision when using the lens. It can also lead to ocular irritation and immunogenicity, due to the eye's sensitization to the foreign protein. For example, Breen reported symptoms of ocular irritation in patients with ocular sensitivity to contact lenses which have been cleaned with the enzyme subtilisin (Breen et al., *Clinical Comparison of Pancreatin-Based and Subtilisin-Based Enzymatic Cleaners*, Contact Lens Forum, volume 15, pages 32–38 (1990)). Consequently, the use of enzyme cleaning is generally limited to a once-per-week regimen. As a result, daily supplemental cleaning, which involves the rubbing of the lens with a surfactant, is necessary to clean the lens satisfactorily during the interim period between the weekly enzymatic cleanings. Thus, the contact lens user is burdened by the purchase of two separate cleaners and the employment of them separately in order to effectively clean his lenses. Therefore, although enzyme cleaning systems provide effective cleaning, they have not been fully exploited as a once-per-day regimen for the optimal cleaning and convenience they would otherwise provide. The modification of the enzyme to hinder its binding to the lens would reduce ocular irritation and immunogenicity, improve visual clarity, and therefore enable a more regular use of the enzyme for cleaning contact lenses.

The use of modified enzymes for use in cleaning various articles has been proposed. For example, enzymes have been modified by altered amino acid sequences, in an effort to decrease adsorption to an insoluble surface and for greater hydrolysis of target proteins; such enzymes have been disclosed in WIPO Publication No. WO 95/07991 (assigned to Procter & Gamble).

Enzymes have also been modified by organic polymer linkage. The covalent linking of proteins with polyethylene glycol (PEG), to yield a polyoxyethylene-protein product, is disclosed by U.S. Pat. No. 4,179,337 (Davis et al.). A variety of publications and patents have described numerous types of PEG-modified proteins and methods of preparation. Davis et al., above, discloses PEG-modified or polypropylene glycol-modified, non-immunogenic polypeptides for use in the circulatory system of the human body. European Patent Application No. 0 584 876 A2 discloses low diol polyalkylene oxide biologically active proteinaceous substances, including a Subtilisin Carlsberg.

Another method of enzyme modification has involved organic monomer linkage to the enzyme. For example, Johansen discloses methods of succinylation and glutarylation of subtilisins in *Chemical Derivatives of Subtilisins with Modified Proteolytic Activities II. Succinyl-and Glutarylsubtilisin Type Carlsberg*, Compt. Renal, Tray. Lab. Carlsberg, volume 37, pages 145–177 (1970).

SUMMARY OF THE INVENTION

The present invention is based in part on the finding that particular modified enzymes exhibit low binding to hydrophilic lenses. The enzymes contained in compositions of the present invention exhibit low isoelectric points relative to physiological pH. Enzymes exhibiting low pIs of the present invention, are prevented from electrostatic attraction to negatively charged hydrophilic lenses. This lower binding of enzymes to the contact lens surface reduces possible ocular irritation of the bound enzyme when the contact lens is reinserted in the eye. The lower binding may also improve enzyme cleaning efficacy. Thus, the present invention has overcome issues of toxicity and efficacy to provide a more effective cleaning system for contact lenses.

The compositions of the present invention are formulated in either solid or liquid form. Compositions formulated in liquid form may, for example, comprise a polyol and an enzyme. The methods of the present invention provide for cleaning of contact lenses with the compositions of the present invention. The methods of the present invention also provide for the simultaneous cleaning and disinfecting of contact lenses, when compositions of the present invention are combined with suitable disinfecting solutions, such as those containing polyquaternium-1.

DETAILED DESCRIPTION OF THE INVENTION

The enzymes of the present invention exhibit low isoelectric points ("pI") relative to physiological pH. This is significant as some hydrophillic contact lenses exhibit a net negative charge at physiological pH. As the enzymes are neutral or have a net negative charge at physiological pH, they will not electrostatically bind to the lenses. Enzymes, especially those from microbial sources, can accumulate in or on lenses and cause ocular irritation when they come into contact with the eye. Therefore, the use of low electrostatically binding enzymes, i.e., those with low pIs, provides a safe and more comfortable method for contact lens cleaning.

As used herein, the term "low pI" refers to electrochemical properties of an enzyme such that the enzyme has a net charge of zero within the pH range of 4-8. The pI of an enzyme can be determined by methods known to those skilled in the art. In general, the use of the technique of isoelectric focusing, as described in Example 3 below, may be used to determine the pI of an enzyme.

The enzymes which may be used in the compositions and methods of the present invention include those enzymes which have been modified to exhibit low pIs, and which: (1) are useful in removing deposits from contact lenses; (2) cause, at most, only minor ocular irritation in the event a small amount of enzyme contacts the eye as a result of inadequate rinsing of a contact lens; (3) are relatively chemically stable and effective in the presence of the antimicrobial agents described below; and (4) do not adversely affect the physical or chemical properties of the lens being treated. For purposes of the present specification, enzymes which satisfy the foregoing requirements are referred to as being "ophthalmically acceptable."

The proteolytic enzymes used herein must have at least a partial capability to hydrolyze peptide-amide bonds in order to reduce the proteinaceous material found in lens deposits to smaller water-soluble subunits.

Examples of native enzymes which may be modified for use in the present invention, include but are not limited to: pancreatin, trypsin, chymotrypsin, subtilisin, collagenase, elastase, keratinase, carboxypeptidase, papain, bromelain, aminopeptidase, Aspergillo peptidase, pronase E (from *S. griseus*) and dispase (from *Bacillus polymyxa*) and mixtures thereof. If papain, or any sulfhydryl protease is used, a reducing agent, such as N-acetylcysteine, may be required.

Microbially derived enzymes, such as those derived from Bacillus, Streptomyces, and Aspergillus microorganisms, represent a preferred type of enzyme to be modified for use in the present invention. Of this sub-group of enzymes, the most preferred are the Bacillus derived alkaline proteases genetically called "subtilisin" enzymes.

Examples of subtilisin enzymes include subtilisin BPN' and subtilisin Carlsberg. Subtilisin is commercially available from various commercial sources including Novo Industries (Bagsvaerd, Denmark), Fluka Biochemika (Buchs, Switzerland) and Boehringer Mannhelm (Indianapolis, Ind.).

The identification, separation and purification of enzymes is known in the art. Many identification and isolation techniques exist in the general scientific literature for the isolation of enzymes, including those enzymes having proteolytic and mixed proteolytic/amylolytic/lipolytic activity. The native enzymes to be modified for use in this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention as long as they meet the criteria for stability, activity and can be modified to exhibit a low pI as set forth herein.

The amount of enzyme used in the compositions of the present invention will range from about 0.01 to 5% w/v, due to various factors, such as purity, specificity and efficacy. The preferred compositions of the present invention will contain a low pI subtilisin in a range of about 0.01 to 1.0% w/v.

The enzymes of the present invention may be selected from those that have had part of their amino acid sequence altered in favor of a lower pI. In general, amino acid residues exhibiting high (net positive charge at physiological pH) pKa's (pH at which half of the total quantity of the particular residue is charged) may be replaced with neutral or low pKa amino acids. For example, lysine or arginine (high pKa) residues may be replaced by alanine, leucine (non-ionic), aspartate, glutamate (low pKa) or other low pKa residues. This can be achieved by traditional genetic recombinant techniques like those described in WIPO Publication No. WO 95/07991 (assigned to Proctor and Gamble), the contents of which pertain to genetic recombinant techniques are incorporated herein by reference. As used herein, "genetic recombinant techniques" refer to any method of producing mutant enzymes of the present invention through the manipulation of DNA. Generally, a plasmid of a host bacterium is transfected with DNA coding for the modified amino acid sequence desired. The plasmid is reinserted in the host, and the host is grown under set conditions. Broth from the fermenting process, containing the bacterial exudate, is then separated from the bacterial colonies and is extracted for the target enzyme. Separation techniques including gel and affinity chromatography are generally employed to purify the mutant type enzymes exhibiting low pIs. Enzymes with lysine residues replaced with lower pI amino acids are preferred modified enzymes of this class of modified enzymes of the present invention.

The enzymes of the present invention may be selected from those that have been chemically modified, covalently, with organic monomer or polymer molecules. As used herein, "organic monomer covalent linkage" refers to the linking of small organic monomers covalently to an enzyme; and "organic polymer covalent linkage" refers to linking large organic polymers covalently to an enzyme. Examples of organic monomers include succinate, and methyl, ethyl or proplyl acylates. Examples of organic polymers include various polyethylene glycols (PEG), such as PEG 500, 1000 and 2000. Such modifications have been discused in U.S. Pat. No. 5,122,614, the entire contents of which are incorporated herein by reference. The use of this technique or similar techniques known to those skilled in the art may be employed to modify various proteases so that they exhibit low pIs and are opthalmically acceptable as set forth above. Commonly assigned U.S. patent application Ser. No. 08/491,754, filed Jun. 19, 1995 discloses novel PEG-subtilisins; the contents pertaining to these novel enzyme-polymer complexes is incorporated herein by reference. Examples of methods for monomeric modifications of enzymes are discussed in Johansen, *Chemical Derivatives of Subtilisins with Modified Proteolytic Activities II. Succinyl- and Glutarylsubtilisin Type Carlsberg, Compt. Rend. Trav. Lab. Carlsberg*, volume 37, pages 145–177 (1970), the entire contents of which, are incorporated herein by reference. Preferred enzymes of this class are succinylated-subtilisins and more generally, acylated-subtilisins.

As it is known to those skilled in the art, the degree of substitution can be controlled by adjusting the ratio of modifying reagent to enzyme concentration. It has been found that enzymes that are modified extensively are less thermally stable in aqueous vehicles (i.e., they may not be easily stabilized in liquid form). Enzymes suitable for liquid stabilized vehicles may require minimal modification whereas all modified enzymes would be useful in a solid form (i.e., effervescent tablets).

The compositions of the present invention may be either in solid or liquid form. Solid forms usually encompass a compressed tablet wherein various excipients are employed. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be incorporated into the enzyme tablet when enzyme tablets are employed.

Examples of suitable buffering agents which may be incorporated into an enzyme tablet include, but are not limited to, alkali metal salts such as potassium or sodium carbonates, acetates, borates, phosphates and citrates, and weak acids such as acetic and boric acids. Preferred buffering agents are alkali metal borates such as sodium or potassium borates. Additionally, other pH adjusting agents may be employed such as inorganic or organic acids and bases. For example, hydrochloric acid, sodium hydroxide, triethanolamine or Tris may be employed in concentrations suitable for ophthalmic uses. Generally, buffering agents are present in amounts from about 0.01 to about 2.5% (w/v) and preferably, from about 0.5 to about 1.5% (w/v), of the working solution.

Effervescing agents are typically employed when the enzyme is provided in solid form. Examples of suitable effervescing agents include, but are not limited to, tartaric or citric acid used in combination with a suitable alkali metal salt such as sodium carbonate.

The tonicity adjusting agent which may be a component of a disinfecting solution and may optionally be incorporated into an enzyme tablet is employed to adjust the osmotic value of the final cleaning and disinfecting solution to more closely resemble that of human tears and to maintain a suitable level for optimum activity by the antimicrobial agent. Typical tonicity adjusting agents are NaCl and KCl.

Suitable surfactants can be either cationic, anionic, non-ionic or amphoteric. Preferred surfactants are neutral or nonionic surfactants which may be present in amounts up to 5% (w/v). Examples of suitable surfactants include, but are not limited to, polyethylene glycol ether or esters of fatty acids, polyoxyethylene-polyoxypropylene block copolymers of ethylene diamine (i.e., poloxamine), polyoxypropylene-polyoxyethylene glycol nonionic block polymers (i.e., polaxamers such as Pluronic F-127) and p-isooctylpolyoxyethylene phenol formaldehyde polymers (i.e, Tyloxapol).

Examples of preferred chelating agents include ethylenediaminetetraacetic acid (EDTA) and its salts (disodium) which are normally employed in amounts from about 0.025 to about 2.0% (w/v). Other known chelating (or sequestering agents) can also be employed.

The binders and lubricants for enzyme tableting purposes and other excipients normally used for producing powders, tablets and the like, may be incorporated into enzyme tablet formulations.

A disinfecting agent may optionally be added to the enzyme tablet. Such disinfectants include those described below in the methods of the present invention.

The above ingredients may be incorporated into tablet form by methods known to those skilled in the art.

Liquid compositions containing low pI modified enzymes are also contemplated by the present invention. Such compositions will be comprised of one or more low pI enzymes of the present invention and a suitable liquid vehicle. As used herein, the term "suitable liquid vehicle" refers to any aqueous or non-aqueous carrier that provides stabilization of the enzyme and preservation of the composition for multiple use dispensing.

Stabilizing agents in the liquid compositions of the present invention will include monomeric and/or polymeric polyols, and optionally, an enzyme inhibitor. As used herein, the term "monomeric polyol" refers to a compound with 2 to 10 carbon atoms and at least two hydroxy groups. Examples of monomeric polyols are glycerol, propylene glycol, ethylene glycol, sorbitol and mannitol. As used herein, the term "polymeric polyol" refers to a polyalkoxylated glycol with a molecular weight ranging from 200–1000. Examples of polymeric polyols are polyethylene glycol 200 (PEG 200) and PEG 400.

The amounts of the components comprising the polyol will vary depending on the particular combination of polyols used. In general, liquid enzyme compositions of the present invention will require 10–70% v/v of at least one polyol to achieve the necessary criteria for efficacious and commercially viable liquid enzyme compositions, as described above. While any of the polyols can be components of the compositions of the present invention, particular polyols may be used depending on the particular intended use. For example, propylene glycol, which has preservative activity, is a preferred monomeric polyol when the need for an additional preservative present in a liquid enzyme composition of the present invention is desired.

The liquid compositions of the present invention may optionally contain a reversible enzyme inhibitor. The inhibitor will be added in an amount necessary to inactivate the enzyme, but where reactivation is easily achieved by dilution of the inhibited enzyme/stabilizing agent complex in an aqueous medium. When the enzyme is in an inactive form, it is prevented from self-degradation and other spontaneous, chemically irreversible events. Examples of reversible inhibitors include borates, phenylboronic acid and lower alkyl carboxylic acids such as propanoic and butyric acids. As used herein, the term "lower carboxylic acid" refers to a compound having a carboxylic acid group and from 2–4 carbon atoms in total. Preferred inhibitors include phenylboronic acid and it derivatives. The preferred range of a phenylboronic acid derivative used in the present invention is 0.1 to 5.0% weight/volume ("% w/v").

A variety of preservatives may be employed to preserve a multi-dispensing liquid enzyme composition of the present invention. In general, any of the agents listed for use in the disinfecting solutions of the methods of the present invention, with the exception of oxidative disinfecting agents, may be employed. Particularly preferred, are the polymeric quaternary ammonium compounds, the most preferred is polyquaternium-1. The amount of preservative used will depend on several factors including the anti-microbial efficacy of the particular agent and any synergistic interaction the agent may have with the liquid enzyme composition. In general, 0.0001 to 0.1% w/v of the preservative agent will be used.

The liquid compositions may contain one or more surfactants selected from anionic, non-ionic or zwitterionic classes. Examples of non-ionic surfactants include alkyl polyoxyethylene alcohols, alkyl phenyl polyoxyethylene alcohols, polyoxyethylene fatty acid esters, polyethylene oxide-polypropylene oxide copolymers such as polaxomers and polaxamines. Examples of anionic surfactants include alkyl sarcosinates and alkyl glutamates. Examples of amphoteric surfactants include alkyliminopropionates and alkylamphoacetates. In general 0 to 5% w/v of the surfactant will be used.

The liquid compositions may contain additional stabilizing agents. These include the stabilizing multi-valent ions, such as calcium and magnesium and their halide salts. Calcium chloride is the most preferred multi-valent stabilizing agent.

Other ingredients may optionally be added to the liquid enzyme compositions of the present invention. Such ingredients include buffering agents, such as, Tris, phosphate or borate buffers; tonicity adjusting agents, such as NaCl or KCl; metal chelating agents, such as ethylenediaminetetraacetic acid (EDTA) and pH adjusting agents such as sodium hydroxide, tris, triethanolamine and hydrochloric acid.

The cleaning methods of the present invention involve the use of an amount of enzyme effective to remove substantially or to reduce significantly deposits of proteins, lipids, mucopolysaccharides and other materials typically found on human-worn contact lenses. For purposes of the present specification, such an amount is referred to as "an amount effective to clean the lens." The amount of liquid enzyme cleaning composition utilized in particular embodiments of the present invention may vary, depending on various factors, such as the purity of the enzyme utilized, the proposed duration of exposure of lenses to the compositions, the nature of the lens care regimen (e.g., the frequency of lens disinfection and cleaning), the type of lens being treated, and the use of adjunctive cleaning agents (e.g., surfactants).

The liquid enzyme compositions of the present invention must be formulated to provide storage stability and antimicrobial preservation suitable for multiple use dispensing, and must provide effective enzymatic activity to breakdown and hence remove proteinaceous, sebaceous, and other foreign deposits on the contact lens. The liquid enzyme compositions must not contribute to the adverse effects of deposit formation on the lens, ocular irritation, or immunogenicity from continuous use. Additionally, when combined with a disinfecting solution containing an antimicrobial agent which is adversely affected by high ionic strength such as polyquaternium-1, the compositions of the present invention must have little or no impact on the ionic strength of the disinfecting solution.

As used in the present specification, the term "low osmolality effect" is defined as an increase in osmolality of about 0-50 milliOsmoles/kg when 1 to 2 drops of the liquid enzyme composition is added to the diluent solution. Osmolality can be an indirect measure of the ionic strength of a solution. It is convenient to utilize osmolality measurements to define acceptable tonicity ranges for disinfecting solutions. As indicated above, the antimicrobial activity of disinfecting agents, particularly polymeric quaternary ammonium compounds such as polyquaternium-1, is adversely affected by high concentrations of sodium chloride or other ionic excipients.

The ionic strength or tonicity of the cleaning and disinfecting solution of the present invention has been found to be an important factor. More specifically, polymeric ammonium compounds, and particularly those of Formula (I), below, lose antimicrobial activity when the concentration of ionic solutes in the disinfecting solution is increased. The use of solutions having low ionic strengths (i.e., low concentrations of ionic solutes such as sodium chloride) is therefore preferred. Such low ionic strengths generally correspond to osmolalities in the range of hypotonic to isotonic, and more preferably in the range of 150 to 350 milliOsmoles per kilogram (mOs/kg). A range of 200 to 300 mOs/kg being is particularly preferred and a tonicity of about 220 mOs/kg is most preferred.

The methods of the present invention utilize a disinfecting solution containing an antimicrobial agent. Antimicrobial agents can be oxidative, such as hydrogen peroxide, or non-oxidative polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polymeric quaternary ammonium compounds, such as disclosed in U.S. Pat. Nos. 3,931,319 (Green, et al.), 4,026,945 (Green, et al.) and 4,615,882 (Stockel, et al.) and the biguanides, as described below. The entire contents of the foregoing publications are hereby incorporated in the present specification by reference. Other antimicrobial agents suitable in the methods of the present invention include: benzalkonium halides, and biguanides such as salts of alexidine, salts of chlorhexidine, hexamethylene biguanides and their polymers. The polymeric antimicrobial agents used herein are preferably employed in the absence of mercury-containing compounds such as thimerosal. The salts of alexidine and chlorhexidine can be either organic or inorganic and are typically gluconates, nitrates, acetates, phosphates, sulphates, halides and the like.

Particularly preferred are polymeric quaternary ammonium compounds of the structure:

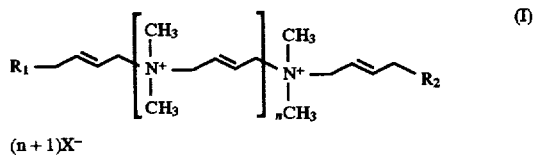

(n+1)X⁻ wherein:

R₁ and R₂ can be the same or different and are selected from:

N⁺(CH₂CH₂OH)₃X⁻, N(CH₃)₂ or OH;

X is a pharmaceutically acceptable anion, preferably chloride; and n=integer from 1 to 50.

The most preferred compounds of this structure is polyquaternium-1, which is also known Onamer M™ (registered trademark of Onyx Chemical Corporation) or as Polyquad® (registered trademark of Alcon Laboratories, Inc.). Polyquaternium-1 is a mixture of the above referenced compounds, wherein X is chloride and R₁, R₂ and n are as defined above.

The above-described antimicrobial agents are utilized in the methods of the present invention in an amount effective to eliminate substantially or to reduce is significantly the number of viable microorganisms found on contact lenses, in accordance with the requirements of governmental regulatory agencies, such as the U.S. Food and Drug Administration. For purposes of the present specification, that amount is referred to as being "an amount effective to disinfect" or "an antimicrobially effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. The type of lens being treated (e.g., "hard" versus "soft" lenses) may also be a factor. In general, a concentration in the range of about 0.000001% to about 0.01% by weight of one or more of the above-described antimicrobial agents will be employed. The most preferred concentration of the polymeric quaternary ammonium compounds of Formula (I) is about 0.001% by weight.

Oxidative disinfecting agents may also be employed in the methods of the present invention. Such oxidative disinfecting agents include various peroxides which yield active oxygen in solution. Preferred methods will employ hydrogen peroxide in the range of 0.3 to 3.0% to disinfect the lens. Methods utilizing an oxidative disinfecting system are described in U.S. Pat. No. Re 32,672 (Huth, et al.) the entire contents of which, are hereby incorporated in the present specification by reference.

As will be appreciated by those skilled in the art, the disinfecting solutions utilized in the present invention may contain various components in addition to the above-described antimicrobial agents, such as suitable buffering agents, chelating and/or sequestering agents and tonicity adjusting agents. The disinfecting solutions may also contain surfactants.

The tonicity adjusting agents, which may be a component of the disinfecting solution and may optionally be incorporated into the liquid enzyme composition, are utilized to adjust the osmotic value of the final cleaning and disinfecting solution to more closely resemble that of human tears. Suitable tonicity adjusting agents include, but are not limited to, sodium and potassium chloride, dextrose, calcium and magnesium chloride, the buffering agents listed above are individually used in amounts ranging from about 0.01 to 2.5% (w/v) and preferably, from about 0.5 to about 1.5% (w/v).

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}$–$C_{18}$ alkanes and polyoxyethylene-polyoxypropylene block copolymers of ethylene diamine (i.e. poloxamine).

Examples of preferred chelating agents include ethylenediaminetetraacetic acid (EDTA) and its salts (e.g., disodium) which are normally employed in amounts from about 0.025 to about 2.0% (w/v).

The methods of the present invention will typically involve adding a small amount of a liquid enzyme composition of the present invention to about 2 to 10 mL of disinfecting solution, placing the soiled lens into the enzyme/disinfectant solution, and soaking the lens for a period of time effective to clean and disinfect the lens. The small amount of liquid enzyme composition can range due to various applications and the amount of disinfecting solution used, but generally it is about 1 to 2 drops. The soiled lens can be placed in the disinfecting solution either before or after the addition of the liquid enzyme composition. Optionally, the contact lenses are first rubbed with a non-enzymatic daily surfactant cleaner prior to immersion in the enzyme/disinfectant solution. The lens will typically be soaked overnight, but shorter or longer durations are contemplated by the methods of the present invention. A soaking time of 4 to 8 hours is preferred. The methods of the present invention allow the above-described regimen to be performed once per week, but more preferably, every day.

The following examples are presented to illustrate further, various aspects of the present invention, but are not intended to limit the scope of the invention in any respect.

EXAMPLE 1

A preferred enzyme composition of the present invention, and a suitable disinfecting solution that may be used in combination with that composition, are described below:

A. Subtilisin Tablet Composition

The following enzyme composition represents a preferred embodiment of the present invention:

| Ingredient | mg/50 mg Tablet |
| --- | --- |
| Succinylated-Subtilisin | 0.1–0.5 |
| Citric Acid | 5.95 |
| Sodium Bicarbonate | 13.135 |
| Povidone (K 29–32) | 0.415 |
| Polyethylene Glycol (3350) | 0.75 |
| Compressible Sugar | QS |
| Alcohol | QS* |

*evaporated during processing

The above ingredients are combined and formed into tablets of appropriate size and hardness, according to methods known to those skilled in the art.

This tablet may also be formulated with a seal coating and/or a delayed release coating to provide for a delay in dissolution of up to about 2 hours.

B. Disinfecting Solution

The following formulation represents a preferred disinfecting solution:

| Ingredient | w/v (%) |
| --- | --- |
| Polyquaternium-1 | 0.001 + 10% excess |
| Sodium chloride | 0.48 |
| Disodium Edetate | 0.05 |
| Citric acid monohydrate | 0.021 |
| Sodium citrate dihydrate | 0.56 |
| Purified water | QS |

To prepare the above formulation, sodium citrate dihydrate, citric acid monohydrate, disodium edetate, sodium chloride and polyquaternium1, in the relative concentrations indicated above, were mixed with purified water and the components allowed to dissolve by stirring with a mixer. Purified water was added to bring the solution to almost 100%. The pH was recorded at 6.3 and adjusted to 7.0 with NaOH. Purified water was added to bring the solution to 100%. The solution was stirred and a pH reading of 7.0 was taken. The solution was then filtered into sterile bottles and capped.

EXAMPLE 2

The method of isoelectric focusing was performed to determine the pI of enzymes. The method of Bio-Rad, as described in Bio-Rad's *Model 111 Mini IEF Cell Instruction Manual*, was followed.

Briefly, a 1 to 2 μl aliquot (5 mg/ml) of one or more proteases to be determined for pI or control proteins of known pIs were applied to a polyacrylamide gel slab containing carrier ampholytes (pH ranging from 3.0 to 10.0). Electrofocusing separation of the proteases in the gel was then carried out with a mini isoelectrofocusing cell (Model III, Bio-Rad Laboratories, Hercules, Calif.) according to the instruction manual provided by the vender. After staining the gel with a dye (Coomassie Brilliant Blue R-250), the protein bands displayed on the gel slab were identified. The pI of each protease was determined based on a calibration curve (pH versus migration distance) established with the control proteins (IEF Standards, a mixture of nine natural proteins with known isoelectric points ranging from 4.45 to 9.60, Bio-Rad). The data of some representative proteases of the present invention, some proteases outside the scope of the present invention and the control proteins is presented in Table 1 below:

TABLE 1

| | | Migration distance on the gel (mm) | |
|---|---|---|---|
| # | Protein | Migration (mm) | PI |
| 1 | Phycocyanin | 4 | 4.6 |
| 2 | β-Lactoglobulin B | 9 | 5.1 |
| 3 | Bovine carbonic anhydrase | 15 | 6.0 |
| 4 | Human carbonic anhydrase | 18 | 6.5 |
| 5 | Equine myoglobin | 22 | 7.0 |
| 6 | Human myoglobin A | 23 | 7.1 |
| 7 | Human myoglobin C | 25 | 7.5 |
| 8 | Lentil lectin | 28 | 8.2 |
| 9 | Cytochrome C | 39 | 9.6 |
| | Subtilisin A (Carlsberg) | 26 | 9.4 |
| | Succinylated subtilisin A | 5 | 4.60 |
| | Acetylated subtilisin A | 4 | 4.45 |
| | PEG-5000-subtilisin BPN' | 4 | 4.45 |
| | Me-PEG-5000-subtilisin A | 4 | 4.45 |
| | Trypsin (Bovine) | 38 | 9.37 |
| | Acetylated Trypsin | 2 | 4.16 |
| | Methylated Trypsin | 39 | 9.51 |

As illustrated in Table 1, succinylation and acylation successfully lowered the pI of subtilisin and trypsin down within the pI range of the present invention.

The invention in its broader aspects is not limited to the specific details shown and described above. Departures may be made from such details within the scope of the accompanying claims without departing from the principles of the invention and without sacrificing its advantages.

What is claimed is:

1. An enzyme composition for cleaning contact lenses comprising a modified enzyme which exhibits a net charge of zero within a pH range of 4 to 8, in a suitable liquid vehicle containing one or more polyols.

2. The composition according to claim 1, wherein the enzyme is modified to exhibit a net charge or zero within a pH range of 4 to 8 by a process selected from the group consisting of: genetic recombinant technology, organic polymer covalent linkage, and organic monomeric covalent linkage.

3. The composition according to claim 1, wherein the enzyme is selected from the group consisting of succinylated-subtilisins and acetylated-subtilisins.

4. A method for cleaning and disinfecting a contact lens comprising:

placing the lens in an aqueous disinfecting solution containing an amount of an antimicrobial agent effective to disinfect the lens;

forming an aqueous disinfectant/enzyme solution by dissolving an enzyme cleaning tablet composition in said disinfecting solution, said cleaning composition comprising a modified enzyme which exhibits a net charge of zero within a pH range of 4 to 8, wherein the enzyme in the disinfectant/enzyme solution is in an amount effective to clean the lens; and soaking the lens in said aqueous disinfectant/enzyme solution for a period of time sufficient to clean and disinfect the lens.

5. The method according to claim 4, wherein the enzyme is selected from the group consisting of succinylated-subtilisins and acetylated-subtilisins.

6. The method according to claim 4, wherein the antimicrobial agent comprises 0.00001% to 0.05% w/v of polyquaternium-1.

7. The method according to claim 5, wherein the antimicrobial agent comprises 0.00001% to 0.05% w/v of polyquaternium-1, and the disinfecting solution has a pH of 7.0.

8. The method according to claim 4, wherein the disinfecting solution comprises:

about 0.5% w/v of sodium chloride;

about 0.05% w/v of disodium edetate;

about 0.02% w/v of citric acid monohydrate;

about 0.6% w/v of sodium citrate dihydrate;

about 0.001% w/v of polyquaternium-1; and water, and has a pH of 7.0.

9. The method according to claim 4, wherein the aqueous disinfecting solution has an osmolality of from 150 to 350 mOsmoles/kg.

10. A method of cleaning a contact lens which comprises:

placing the lens in an aqueous solution;

forming an aqueous enzyme solution by dissolving an enzyme cleaning tablet composition in said solution, said cleaning composition comprising an enzyme which exhibits a net charge of zero within a pH range of 4 to 8, wherein enzyme in the aqueous enzyme solution is in an amount effective to clean the lens; and soaking the lens in the enzymatic cleaning composition for a period of time sufficient to clean the lens.

11. The method according to claim 10, wherein the enzyme is selected from the group consisting of succinylated-subtilisins and acetylated-subtilisins.

12. An enzyme composition for cleaning contact lenses comprising a modified enzyme which exhibits a net charge of zero within a pH range of 4 to 8, in a solid tablet formulation.

13. A method for cleaning and disinfecting a contact lens comprising:

placing the lens in an aqueous disinfecting solution containing an amount of an antimicrobial agent effective to disinfect the lens;

forming an aqueous disinfectant/enzyme solution by dissolving a liquid enzyme cleaning composition in said disinfecting solution, said cleaning composition comprising a modified enzyme which exhibits a net charge of zero within a pH range of 4 to 8, in a suitable liquid vehicle containing one or more polyols; wherein the enzyme in the disinfectant/enzyme solution is in an amount effective to clean the lens; and soaking the lens in said aqueous disinfectant/enzyme solution for a period of time sufficient to clean and disinfect the lens.

14. A method of cleaning a contact lens which comprises:

placing the lens in an aqueous solution;

forming an aqueous enzyme solution by dispersing a liquid enzyme cleaning composition in said solution, said cleaning composition comprising an enzyme which exhibits a net charge of zero within a pH range of 4 to 8, in a suitable liquid vehicle containing one or more polyols; wherein the enzyme in the aqueous enzyme solution is in an amount effective to clean the lens; and soaking the lens in the aqueous enzyme composition for a period of time sufficient to clean the lens.

* * * * *